(12) United States Patent
Iwasaki et al.

(10) Patent No.: US 6,649,361 B1
(45) Date of Patent: Nov. 18, 2003

(54) SURFACE PLASMON RESONANCE ENZYME SENSOR

(75) Inventors: Yuzuru Iwasaki, Atsugi (JP); Osamu Niwa, Atsugi (JP)

(73) Assignee: Nippon Telegraph and Telephone Corporation (JP)

( * ) Notice: Subject to any disclaimer, the term of this patent is extended or adjusted under 35 U.S.C. 154(b) by 270 days.

(21) Appl. No.: 09/697,356

(22) Filed: Oct. 27, 2000

(30) Foreign Application Priority Data

Oct. 28, 1999 (JP) .......................................... 11-306296

(51) Int. Cl.[7] .......................................... G01N 33/573
(52) U.S. Cl. ................... 435/7.4; 356/317; 356/318; 356/445; 356/447; 385/12; 385/129; 385/130; 422/82.01; 422/82.02; 422/82.05; 422/82.09; 422/82.11; 435/176; 435/287.1; 435/288.7; 436/164; 436/165; 436/518; 436/524; 436/525; 436/527; 436/805
(58) Field of Search ................... 422/82.01, 82.02, 422/82.05, 82.09, 82.11; 436/164, 165, 805, 518, 524, 525, 527; 435/287.1, 288.7, 176, 7.4; 204/403; 356/317, 318, 445, 447; 385/12, 129, 130

(56) References Cited

U.S. PATENT DOCUMENTS

| | | | | |
|---|---|---|---|---|
| 4,844,613 A | * | 7/1989 | Batchelder et al. | ......... 356/318 |
| 5,858,799 A | | 1/1999 | Yee et al. | |
| 6,387,614 B1 | * | 5/2002 | Cheng et al. | ................... 435/4 |

FOREIGN PATENT DOCUMENTS

DE 19824629 12/1999

OTHER PUBLICATIONS

Vreeke, Maidan, Heller; Anal. Chem. 1992, 64, 3084–3090 (1992), 7 pages.

Kyoritsu Shuppan, May 1986, pp. 26–29 and 33–34.

* cited by examiner

Primary Examiner—Christopher L. Chin
(74) Attorney, Agent, or Firm—Burns, Doane, Swecker, Mathis, LLP

(57) ABSTRACT

A surface plasmon resonance enzyme sensor including a sensing part 6 having an optically transparent base 1, a thin metal film 2 made of gold or silver, and a film 4 provided on the metal thin film 2 causing electron transfer reaction with both the thin metal film and the enzyme is provided.

4 Claims, 4 Drawing Sheets

SURFACE PLASMON RESONANCE ENZYME SENSOR

BACKGROUND OF THE INVENTION

1. Field of the Invention

The present invention relates to a surface plasmon resonance enzyme sensor and a method of measuring surface plasmon characterized by performing measurement of surface plasmon resonance with electrochemical oxidoreduction activity using an enzyme.

2. Description of the Prior Art

Biosensors using enzymes have been widely investigated as means for selectively detecting blood glucose level and a number of biomolecules such as cholesterol, urea and vitamins (cf., for example, Isao Karube, "Biosensor", published by Kyoritsu Shuppan, May 2, 1986). In particular, combinations of an oxidase and an electrochemical detection method have been extensively studied. For example, combinations of a blood glucose level sensor and a urea glucose level sensor are commercially available from several manufacturers.

In the case of sensors using oxidases, several combinations as shown in FIG. 3 are known, which are roughly classified into the following:

(1) Methods in which a decrease in oxygen concentration with consumption of oxygen upon enzymatic reaction is measured by an oxygen sensor;
(2) Methods in which hydrogen peroxide, which is a product of enzymatic reaction, is electrically oxidized for detection;
(3) Methods in which a redox molecule called electron mediator and an enzyme are mixed or chemically coupled and the enzyme is reacted on an electrode through the electron mediator (without oxygen consumption), etc. have been known.

As intermediate methods between (2) and (3), (4) Methods in which hydrogen peroxide generated in an enzymatic reaction is reduced through horseradish peroxidase (HRP) electrically coupled to electron mediators (cf., for example, Vreeke, M., Maiden, R., Heller, A., Anal. Chem., 64, 3084–3090 (1992)), also have been known.

On the other hand, biosensors using optical methods have been studied. To detect the product of oxidase, chemiluminescence from the mixture of the product and chemicals such as luminol are widely used.

Recently, sensors utilizing surface plasmon resonance (SPR) have been studied as a biosensor using optical methods. The surface plasmon resonance enzyme sensors (hereinafter, referred to as SPR sensors) can detect a change in refractive index in the range of several hundreds nm from the surface of a base metal such as gold or silver. In actual measurements, the base metal is illuminated at a certain incident angle on the opposite surface of a sample and the angle at which its evanescence wave and surface plasmon resonate is measured.

The schematic of an optical system for measurement is shown in FIG. 4(a). A light beam from an optical source is condensed into a wedge-form light beam, which enters a semi-cylindrical prism 7. The sensing part 6' is attached to the bottom of the prism 7 using a material for matching the refractive indices (matching oil). The incidence light illuminates the sensing part 6' with angles of total reflection conditions. The evanescent wave and surface plasmon wave, which occur on the metal thin film side, will resonate at a certain angle of incidence (surface plasmon resonance). This phenomenon is observed as weak reflection at the resonance angle. When the reflected light is observed by a CCD camera, a valley of reflectivity is measured as shown in FIG. 4(b).

Since the angle at which resonance occurs depends on the optical property (refractive index) of the surface, a molecule bound to the surface of the sensing part 6' changes the refractive index of the surface so that the angle at which a valley appears changes. Measurement of such a change enables high speed monitoring of the interaction between molecules on the surface.

SPR sensors are finding application to immunological sensors utilizing antigen-antibody reaction, DNA detection, receptor-protein interaction detection, etc.

However, among the conventional biosensors, electrochemical enzyme sensors, which conduct measurements using electrodes, require time and hand for a single measurement so that it is difficult for them to measure a large number of samples quickly.

Also, in the case of enzyme sensors utilizing optical methods, it is necessary to add a reagent when measuring chemiluminescence or fluorescence. This makes for a cumbersome operation and requires extra hands and/or expensive analytical apparatus.

Since, the principle of conventional SPR sensors are based on a refractive index change caused by a binding of analytes to the immobilized molecular recognition molecules on the sensing part, the refractive index change of the SPR sensor cannot be made higher than the density of molecule recognition molecule so that there is a limitation in its measurement sensitivity. Furthermore, in the conventional SPR measurement method, it is necessary that the molecule recognition molecule and the molecule to be measured bind to each other. Therefore, the method is difficult to apply to the detection of molecules to be measured having weak binding affinity or short binding lifetime for molecule recognition molecule, for example, binding of enzymes and low molecular compounds such as hydrogen peroxide, benzene derivatives, nitrogen oxides, nerve transmitter substances, amino acids, antigens, DNA oligomers, etc. and there has been the problem that its application range is limited.

SUMMARY OF THE INVENTION

The present invention has been proposed in view of the above and an object of the present invention is to provide a novel principle of measurement and an improved surface plasmon resonance enzyme sensor and a method of measuring surface plasmon resonance.

In one aspect of the surface plasmon resonance enzyme sensor of the present invention, the sensor comprises a sensing part having an optically transparent base plate, a thin metal film made of gold or silver, and a film provided on the metal thin film causing an electron transfer reaction with both the thin metal film and an enzyme.

In the surface plasmon resonance enzyme sensor, the film causing electron transfer reaction may be a polymer film.

In the surface plasmon resonance enzyme sensor, the film causing electron transfer reaction may contain an enzyme, which donates and receives charge to or from the thin metal film therethrough.

The surface plasmon resonance enzyme sensor may comprise at least one selected from the group consisting of enzymes, cells, and microorganisms which have the property of producing a molecule which causes redox reaction with the film which causes electron transfer reaction in at least one manner selected from directly, through the enzyme contained in the film, and both.

In one embodiment of the surface plasmon resonance enzyme sensor of the present invention, the sensor comprises:

an electrochemical cell (10) including a sensing part (6) comprising a glass base plate (1), a thin gold film (2) provided on one surface of the glass base plate(1), a working electrode (3a) provided on the thin gold film (2), a redox polymer film (4) provided on the thin gold film (2) and an enzyme-immobilized film (5) provided on the polymer film (4), a prism (7) provided on the other surface of the glass base plate (1), a jig (9) provided in contact with the thin gold film (2) having a space for holding an electrolyte through a gasket (8) provided with a hole (8a) serving as the working electrode (3a); and a counter electrode (11) and a reference electrode (12) arranged remote from each other in contact with the electrolyte held in the electrochemical cell;

wherein the working electrode (3a), counter electrode (11) and reference electrode (12) are connected to a potentiostat so that electrochemical measurement and surface plasmon resonance measurement can be conducted simultaneously.

In one aspect of the method of measuring surface plasmon resonance according to the present invention, the method comprises the steps of:

using the surface plasmon resonance enzyme sensor as described above, applying predetermined potentials to respective electrodes to produce a change of state of a substance on a surface of the sensing part (6) by electrochemical redox activity, and detecting at least one of changes in the electronic state of molecules, the state of assemblage of molecules, the state of chemical bonding and mass transfer of the substance on the surface of the sensing part (6) by illuminating the sensing part (6) through the prism (7) and measuring the angle at which the resulting evanescent wave and surface plasmon resonate.

In another aspect of the surface plasmon resonance enzyme sensor of the present invention, the sensor comprises a sensing part having an optically transparent base and a thin film provided on at least a part thereof containing a substance which is capable of causing surface plasmon resonance, wherein the thin film is modified with a substance which electrochemically reacts with the thin film or a conductor provided on the thin film and with an enzyme. The configuration of the sensing part is not limited. The material of the thin film is not limited as far as it causes surface plasmon resonance.

In the surface plasmon resonance enzyme sensor, the thin film may be a polymer. A portion of the thin film may participate in redox reaction. Preferably, the polymer contains protein or DNA.

In the surface plasmon resonance enzyme sensor, the thin film may be a thin gold film or a thin silver film. Thus, the thin film may be a single material such as a thin polymer film or a thin metal film. Furthermore, it may be constructed from a thin metal film and a thin polymer film or from a thin metal film, a thin polymer film and one or more thin films made of other components.

In the surface plasmon resonance enzyme sensor, the thin film may contain an enzyme which donates and receives charge to or from the film therethrough.

In the surface plasmon resonance enzyme sensor, the sensor may comprise at least one selected from the group consisting of enzymes, cells, and microorganisms which have a property of producing a molecule which causes a redox reaction with the film which causes electron transfer reaction in at least one manner selected from directly, through the enzyme contained in the film, and both.

In one embodiment of the surface plasmon resonance enzyme sensor of the present invention, the sensor comprises:

an electrochemical cell (10) including a sensing part (6) comprising a glass base (1), a thin gold film (2) provided on one surface of the glass base (1), a working electrode (3a) provided on the thin gold film (2), a redox polymer film (4) provided on the thin gold film (2) and an enzyme-immobilized film (5) provided on the polymer film (4), a jig (9) provided in contact with the thin gold film (2) having a space for holding an electrolyte through a gasket (8) provided with a hole (8a) serving as the working electrode (3a); and a counter electrode (11) and a reference electrode (12) arranged remote from each other in contact with the electrolyte held in the electrochemical cell;

wherein the working electrode (3a), counter electrode (11), and reference electrode (12) are connected so that electrochemical measurement and surface plasmon resonance measurement can be conducted simultaneously.

In another aspect of the method of measuring surface plasmon resonance according to the present invention, the method comprises the steps of:

using the surface plasmon resonance enzyme sensor as described above, applying predetermined potentials or sequence of potentials to the respective electrodes to cause the redox polymer film (4) or enzyme-immobilized film (5) to allow an electrochemical reaction to thereby produce a change of state of a substance on a surface of the sensing part (6); and detecting at least one of the changes in the electronic state of molecules, the state of assemblage of molecules, the state of chemical bonding, and mass transfer of the substance on the surface of the sensing part (6) by illuminating the sensing part (6) through the glass base (1) from the opposite side to the thin gold film, and measuring the angle at which the resulting evanescent wave and surface plasmon resonate.

According to the present invention, measurements of surface plasmon resonance while causing electrochemical oxidoreduction activity using an enzyme enables a single measurement to be carried out in a short time and makes it possible to conduct speedy measurements of a large number of samples.

Also, according to the present invention, the operations in measurement are simplified to save manpower, and an inexpensive analytical apparatus can be constructed.

Furthermore, according to the present invention, it is possible to perform measurements without trapping molecules to be measured by the sensing part so that those molecules to be measured which have weak binding affinity or short binding lifetime for molecule recognition molecules that have been difficult to detect by the conventional SPR methods, such as binding of enzymes and low molecular compounds such as hydrogen peroxide, can be detected at high sensitivity. Therefore, according to the present invention, variation of the kind of molecules to be measured can be broadened.

Moreover, according to the present invention, since measurements can be performed without trapping molecules to be measured by the sensing part, final sensitivity is independent of the density of the substance to be measured so that the sensitivity of measurement can be increased greatly.

DESCRIPTION OF THE PREFERRED EMBODIMENTS

The present inventors have made extensive investigation for realizing a biosensor utilizing an enzyme which uses optical methods but contains neither fluorescent agent nor luminescent agent. As a result they have found that when hydrogen peroxide which will be a product of enzymatic reaction, oxidizes a redox polymer film using horseradish peroxidase (HRP), hydrogen peroxide can be measured in high sensitivity by SPR sensor. Furthermore, the redox polymer film once oxidized can be readily reversed to a reduced state electrochemically, and at the same time the resonance angle of SPR is also reversed to the original position. The present invention is based on these discoveries.

Hereinafter, the present invention will be described in more detail by examples with reference to the attached drawings. However, the present invention should not be construed as being limited to the examples below.

EXAMPLE 1

Figure 1A:
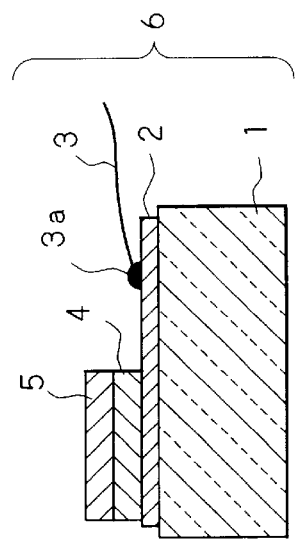
FIG. 1(a) is a schematic diagram showing a sensing part of a surface plasmon resonance enzyme sensor according to one embodiment of the present invention.
Figure 1B:
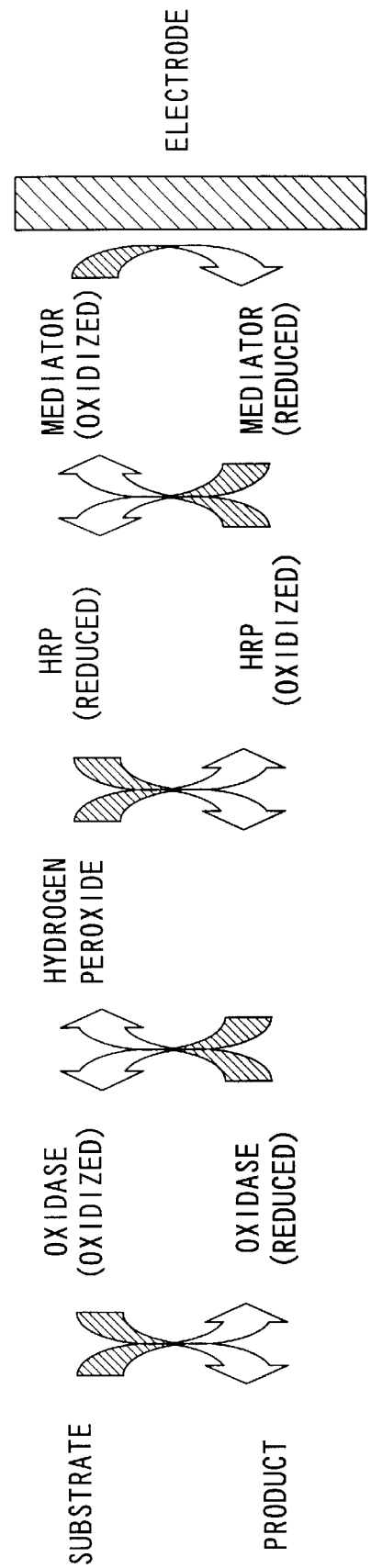
FIG. 1(b) is a schematic diagram illustrating the reaction.

An example of the present invention will be described with reference to the attached drawings. FIG. 1(a) is a schematic diagram for illustrating a sensing part 6 of the surface plasmon resonance enzyme sensor of the present invention and FIG. 1(b) is a schematic diagram for illustrating the reaction on the surface plasmon resonance enzyme sensor. In FIG. 1(a), reference numeral 1 stands for an optically transparent base plate, for example a glass plate made of BK7. Reference numeral 2 stands for a thin metal film made of gold or silver formed on the upper surface thereof. In this example, a thin gold film was used. Reference numeral 3 stands for a lead wire of a working electrode 3a provided on the thin gold film 2. Reference numeral 4 stands for a redox polymer film containing horseradish peroxidase (HRP) provided on the thin gold film 2 and reference numeral 5 stands for an enzyme-immobilized film provided thereon. These elements constitute the sensing part 6 of the surface plasmon resonance enzyme sensor.

Figure 2A:
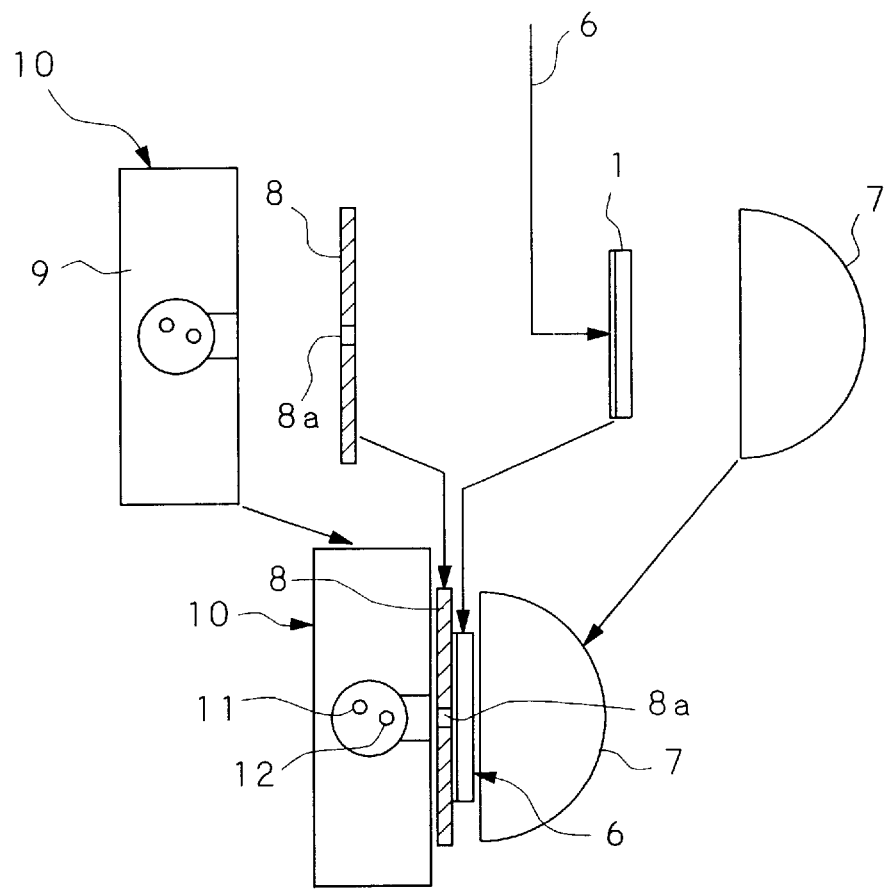
FIG. 2(a) is a diagram showing an electrochemical cell, which detects the substrate of an enzyme in combination with electrochemical reaction using an SPR sensor having an enzyme film.
Figure 2B:
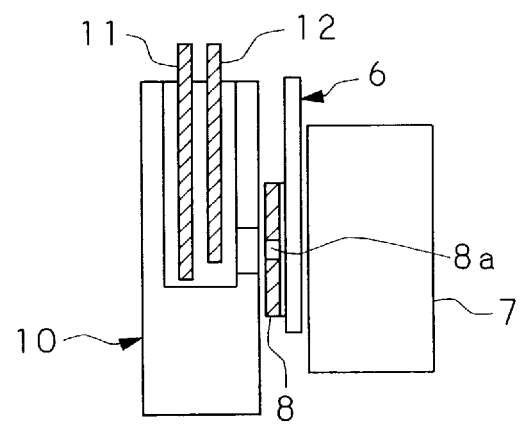
FIG. 2(b) is a diagram showing said cell.
Figure 3:
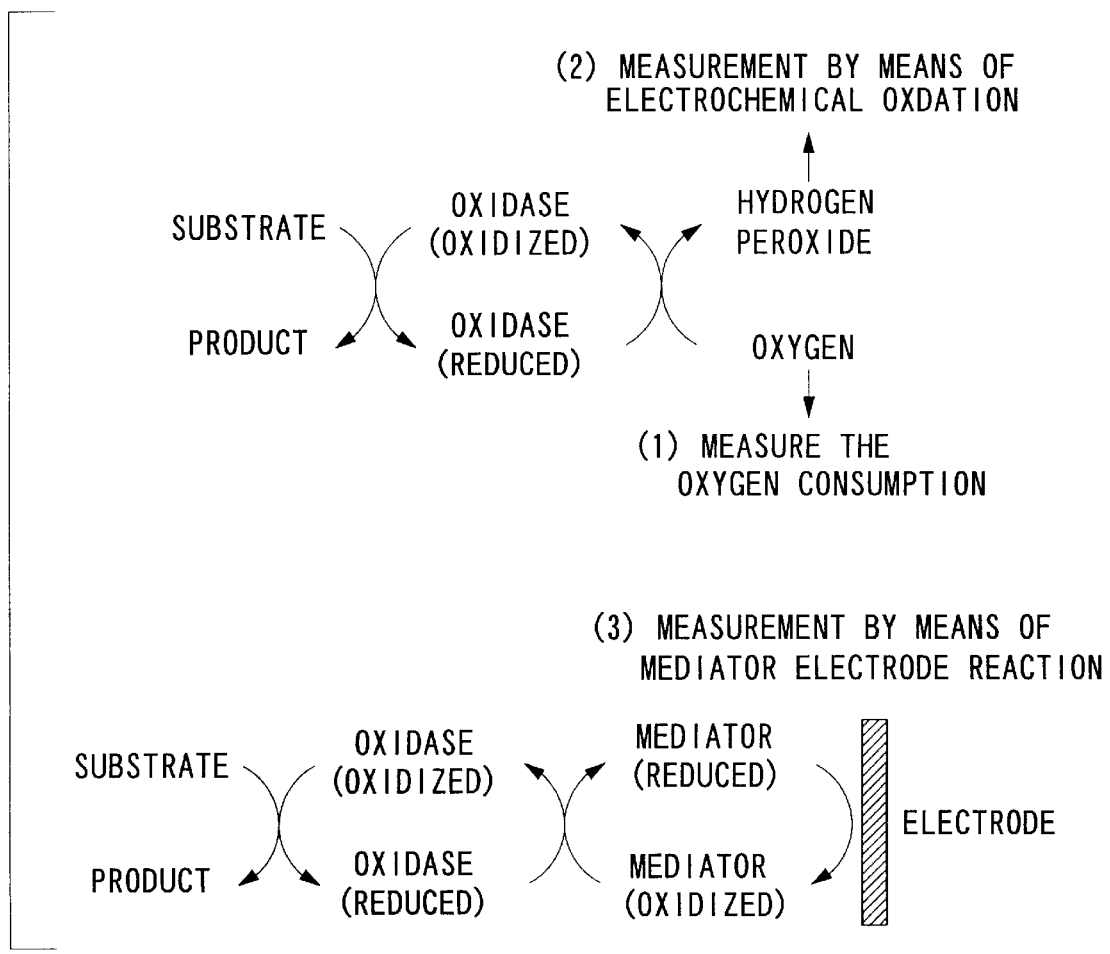
FIG. 3 is a schematic diagram illustrating various measurement methods.

FIGS. 2(a) and (b) shows an electrochemical cell, which detects the substrate of an enzyme in combination with electrochemical reaction using an SPR sensor having an enzyme film.

The cell indicated by reference numeral 10 was fabricated as follows. The thin gold film 2 was formed on one surface of the glass base plate 1, for example, glass base plate 1 made of 0.3-mm glass plate manufactured by Matsunami Glass Industry Co., Ltd. (Japan). In this example, the thin gold film 2 of 50 nm thick was formed by a sputtering method using the apparatus manufactured by Nippon Seed Laboratories (Japan). On the thin gold film 2, a redox polymer containing horseradish peroxidase (HRP) (Osmium polymer, manufactured by BAS) is coated to fabricate a biosensor electrode for detecting hydrogen peroxide. The redox polymer film 4 may be any compound as far as it causes electron transfer reaction with both the electrode and enzyme. Besides osmium compounds, substances that serve as electron mediators in biosensors, such as ferrocene compounds, organic redox reagents, metal complexes, and redox enzymes may be utilized.

The redox polymer film 4 having electrochemical redox activity has a property of producing a molecule, which causes a redox reaction with the film, which then causes electron transfer reaction in at least one manner selected from directly, through the enzyme contained in the film, and both. As the above enzyme, those enzymes, which have been well known in the art, may be used. For example, various enzymes described in "1. Redox Enzymes" of "Enzyme Handbook" (Asakura Shoten, 1982), those enzymes described in Enzyme Handbook 10, Class 1.1.1.150–1.1.99.26 Oxidoreductases (Eds.: D. Schomburg, D. Stephan, Springer-Verlak 1995), preferably peroxidases, glucose oxidases, glutamate oxidases, histamine oxidases, choline oxidases, cholesterol oxidases, etc. may be cited. As a substitute for the enzymes, cells or microorganisms producing the enzymes may be used without sufficiently performing isolation or purification of enzymes or as unpurified. The cells used for this purpose include animal brain cells, plant tissue cells, etc., preferably those cells, which produce the above enzymes. The above microorganisms include *Escherichia coli, Bacillus subtilis*, algae, etc., preferably recombinant *Escherichia coli* cells that can synthesize the above enzymes. Moreover, as the substitute for enzymes, those molecules produced by molecular imprint method or catalytic antibody method can be used.

On the other glass surface of the glass base plate 1, which constituted the electrode, a liquid having the same refractive index as BK7 was coated, and then the glass base plate 1 was contacted on the prism 7 of SPR measuring apparatus SPR-20 manufactured by Denki Kagaku Kogyo Co., Ltd. (Japan). Onto a surface of the enzyme-immobilized film 5 of the electrode, a jig 9 having a space for holding an electrolyte through a silicone rubber gasket 8 provided with a circular hole 8a was pressed to construct an electrochemical cell 10. A lead wire 3 was attached to the thin gold film 2, the portion of the hole 8a of the gasket 8 was used as the working electrode 3a. Furthermore, a platinum wire serving as a counter electrode and a silver-silver chloride electrode with a salt bridge serving as a reference electrode 12 were incorporated in the electrochemical cell 10, and an electrolyte was charged in the cell 10 to construct an SPR measurement apparatus. As the electrolyte, aqueous solutions of respective metal salts, ammonium salts, or tris (tris (hydroxylmethyl)aminomethane) salts of phosphoric acid, cacodylic acid, perchloric acid, hexafluorophosphoric acid, tetrafluorophosphoric acid, organic acids, etc. preferably phosphate buffer and tris buffer, can be used.

Figure 4A:
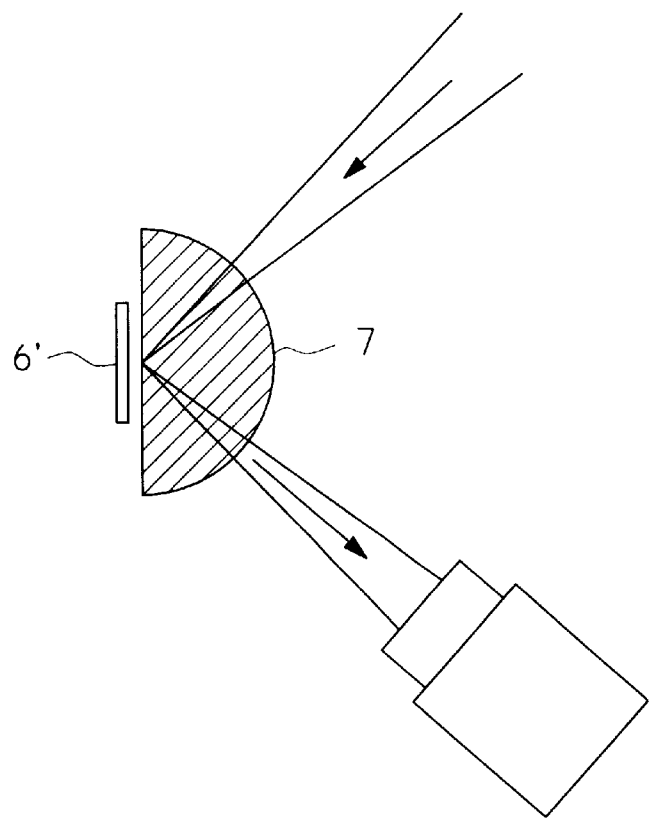
FIG. 4(a) is a schematic diagram showing an optical system for SPR measurements.
Figure 4B:
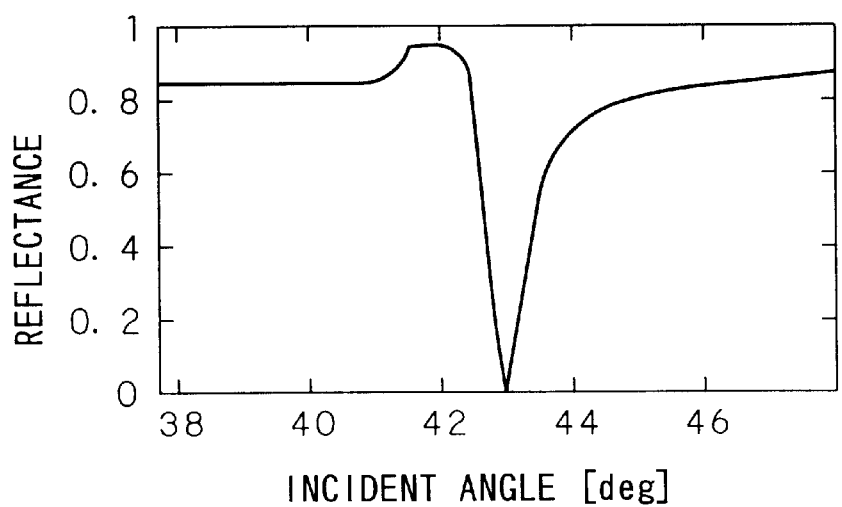
FIG. 4(b) is a schematic diagram showing the state where the intensity of reflected light is measured by a CCD camera.

In the electrochemical cell 10, phosphate buffer was filled, the working electrode lead wire 3, counter electrode 11 and reference electrode 12 were connected to the potentiostat manufactured by Fuso Seisakusho (Japan). Then, the potential at which HRP enzyme activity would appear was applied to the working electrode 3a and electrochemical measurements were performed. At the same time, SPR measurements were performed by SPR-20 as shown in FIGS. 4(a) and 4(b). In the apparatus, measurements were performed by a cyclic voltametry method (hereinafter, referred to as CV) under conditions where no substrate for HRP was contained. As a result, electrochemical current and SPR signal depending on the electrode potential and reaction of mediator were obtained.

Next, CV was performed under conditions where hydrogen peroxide, which was a substrate for HRP, was contained. As a result, a sigmoid curve characteristic of the enzyme reaction was obtained. In the SPR measurement, a change in signal was observed at the same potential as the CV. Therefore, the SPR measurement of the sensing part 6 of the surface plasmon resonance enzyme sensor having the above structure enabled measurements of the electrochemical state of enzyme sensor, that is, changes in the electronic state of molecules, the state of assemblage of molecules, the state of chemical bonding and mass transfer of the substance on the surface of the sensing part 6.

EXAMPLE 2

In the same manner as in Example 1, an electrochemical reaction type biosensor containing HRP was fabricated and an electrochemical SPR measurement apparatus was constructed. A potential at which enzyme activity of HRP would appear was applied to the thin gold film 2 serving as the working electrode 3a. The electrode 3a current and SPR signal were measured with different concentrations of hydrogen peroxide, i.e. the substrate of HRP.

As a result, when the concentration of hydrogen peroxide was low, the current was proportional to the concentration. This revealed that it worked as a sensor. The SPR signal was also proportional to the concentration, and thus quantitative measurements can be realized by SPR measurements. Furthermore, returning the electrochemical cell 10 in the solution containing no substrate, the response by the sensor was returned to the original state. This indicated that repeated measurements could be performed using a simple and easy method.

Next, in the case where the working potential was held at a potential at which no enzyme activity of HRP occurred, the response of the sensor to the concentration of hydrogen peroxide was not obtained by measurement of current or SPR measurement.

Therefore, it revealed that the response of the sensor to hydrogen peroxide obtained by the SPR measurement does not indicate the detection of a change in refractive index on the surface of thin gold film due to a change in concentration of hydrogen peroxide but rather indicates the detection of a change in refractive index of the redox polymer film 4 containing an enzyme caused by the influence of enzyme reaction activated by electrochemical action by the SPR method.

EXAMPLE 3

In the same manner as in Example 1, the sensing part 6 of the surface plasmon resonance enzyme sensor was fabricated and the electrode potential was set such that HRP was in an active state in a solution containing no substrate to HRP. In this case, no current flowed in the electrode and the response of the SPR measurement apparatus was of a constant value.

In this state, a substrate was added and a change in electrode potential in the state where no current flowed (rest potential) was measured. As a result, there was observed a change in potential with time attributable to a change in concentration ratio of the oxidized type and the reduced type of the redox polymer film 4 in which HRP consumed the substrate to cause redox reaction.

In the SPR measurement performed simultaneously, there was observed a change in refractive index reflecting the concentration ratio of the oxidized type and the reduced type. In this case, no potentiostat was necessary at the time of measurement, and a surface plasmon resonance enzyme sensor using a polymer film having a redox activity could be constructed by a more simple method.

EXAMPLE 4

First, the sensing part 6 of the surface plasmon resonance enzyme sensor coated with a redox polymer containing HRP was fabricated in the same manner as in Example 1. On the redox polymer film 4, a glucose oxidase (GOD) containing bovine albumin (Sigma) was coated, and the sensing part 6 was exposed to the vapor of glutaraldehyde (Sigma) to form a GOD-immobilized film layer 5.

To the respective electrodes of the sensing part 6 of the surface plasmon resonance enzyme sensor, potentials were applied such that HRP enzyme activity could be obtained in the same manner as in Example 2 and response of the sensor to glucose was examined.

As a result, the current increased with the concentration of glucose. In the SPR measurement, results, which corresponded to this, were obtained. The detection limit of SPR measurement was $10^{-5}$ M or less so that a sensitivity sufficient for practical purposes could be obtained.

Responses similar to this example were observed when other oxidase films, such as glutamate oxidase, histamine oxidase (Y-H. Choi, R. Matsuzaki, T. Fukui, E. Shimizu, T. Yorifuji, H. Sato, Y. Ozaki and K. Tanizawa, J. Biol. Chem., 270, 4712–20 (1995)), choline oxidase, and cholesterol oxidase films were used. This revealed that a wide variety of enzyme sensors utilizing the SPR method could be constructed.

What is claimed:

1. A surface plasmon resonance enzyme sensor comprising a sensing part having an optically transparent base plate, a thin metal film made of gold or silver formed on a surface of the base plate, a redox film formed on the thin metal film on an opposite surface to the base plate, and an enzyme immobilized or contained on or in the redox film, said redox causing an electron transfer reaction with both the thin metal and the enzyme.

2. The surface plasmon resonance enzyme sensor as claimed in claim 1, wherein the film formed on the thin metal film and causing an electron transfer reaction is a polymer film.

3. The surface plasmon resonance enzyme sensor as claimed in claim 1, wherein the film causing an electron transfer reaction contains an enzyme which donates and receives charges to or from the thin metal film therethrough.

4. The surface plasmon resonance enzyme sensor as claimed in claim 1, further comprising another film formed on the redox film on an opposite surface to the thin metal film, wherein said another film is immobilized and includes material selected from the group consisting of enzymes, cells, and microorganisms which have the property of producing a molecule which causes a redox reaction with the redox film that causes an electron transfer reaction in at least one manner selected from directly, through the enzyme contained in the film.

* * * * *